United States Patent [19]

Parker et al.

[11] Patent Number: 5,565,562
[45] Date of Patent: *Oct. 15, 1996

[54] TRIAZA MACROCYCLES

[75] Inventors: David Parker, Durham; Nigel R. A. Beeley, Thame; Thomas A. Millican, Maidenhead, all of United Kingdom

[73] Assignee: Celltech Therapeutics Limited, Slough, United Kingdom

[*] Notice: The term of this patent shall not extend beyond the expiration date of Pat. No. 5,247,075.

[21] Appl. No.: 467,913

[22] Filed: Jun. 6, 1995

Related U.S. Application Data

[60] Continuation of Ser. No. 948,508, Sep. 18, 1992, abandoned, which is a division of Ser. No. 817,999, Jan. 9, 1992, abandoned, which is a continuation of Ser. No. 601,700, filed as PCT/GB90/00219, Feb. 12, 1990, abandoned.

[30] Foreign Application Priority Data

Feb. 10, 1989 [GB] United Kingdom ................ 8903024
Feb. 10, 1989 [GB] United Kingdom ................ 8903025

[51] Int. Cl.$^6$ ................................................ C07D 255/02
[52] U.S. Cl. ............................................. 540/465; 540/474
[58] Field of Search .................................... 540/465, 474

[56] References Cited

U.S. PATENT DOCUMENTS

| | | | |
|---|---|---|---|
| 4,174,319 | 11/1979 | Kobuke | 260/239 |
| 4,174,428 | 11/1979 | Tabushi et al. | 540/474 |
| 4,432,907 | 2/1984 | Wieder et al. | 436/500 |
| 4,472,509 | 9/1984 | Gansow et al. | 436/538 |
| 4,659,839 | 4/1987 | Nicolotti et al. | 548/546 |
| 4,671,958 | 6/1987 | Rodwell et al. | 514/2 |
| 4,678,667 | 7/1987 | Meares | 424/85 |
| 4,877,600 | 10/1989 | Bonnemain et al. | 257/2 |
| 4,885,363 | 12/1989 | Tweedle et al. | 540/465 |
| 5,049,667 | 9/1991 | Schaefer et al. | 540/474 |
| 5,053,503 | 10/1991 | Dean et al. | 540/474 |
| 5,132,409 | 7/1992 | Felder et al. | 540/465 |
| 5,247,075 | 9/1993 | Parker et al. | 540/465 |
| 5,374,416 | 12/1994 | Rousseaux et al. | 424/2 |

FOREIGN PATENT DOCUMENTS

| | | |
|---|---|---|
| 76217/87 | 2/1988 | Australia . |
| 0173629 | 3/1986 | European Pat. Off. . |
| 0188256 | 7/1986 | European Pat. Off. . |
| 0232751 | 8/1987 | European Pat. Off. . |
| 0255471 | 2/1988 | European Pat. Off. . |
| 88/08422 | 11/1988 | WIPO . |
| 89/01476 | 2/1989 | WIPO . |

OTHER PUBLICATIONS

Khaw et al, *Science.* 209, 295 (1980).

Krejcarek et al., *Biochem. Biophys. Res. Comm.*, 77, 581 (1977).

Childs, R. L. and Hnatowich, D. J., *J. Nuc. Med.* 26, 293 (1985).

Stetter, H., et al., *Angew. Chem. Int. Ed. Engl.*, 15, 686 (1976).

Loncin, J. F., et al., *Inorg. Chem.*, 25, 2646 (1986).

Moi, C. F., et al., *J. Am. Chem. Soc.*, 110, 6266 (1988).

Tweedle, M. F., et al., *J. Nuc. Med.*, 28, 705 (1987).

Goodwin, C. H., et al., *J. Nuc. Med.*, 27, 959 (1986).

Paik, C. H., et al., *J. Nuc. Med.*, 28, 572 (1987).

Paik, C. H., et al., *J. Nuc. Med.*, 29, 889 (1988).

Haseman, C. F., et al., *Eur. J. Nuc. Med.*, 12, 455 (1986).

Parker et al., *Pure & Appl. Chem.*, vol. 61, No. 9, 1637–1641 (1989).

Craig et al., *J. Chem. Soc. Chem. Commun.* (1989), pp. 794–796.

Cox et al., *J. Chem. Soc. Chem. Commun.* (1989), pp. 797–798.

Paik et al., *J. Nucl. Sci.*, vol. 30, No. 10, pp. 1693–1701 (Oct. 1989).

Paik et al., *Nucl. Med. Biol.*, vol. 16, No. 5, pp. 475–481 (1989).

Deshpande et al., *Nucl. Med. Biol.*, vol. 16, No. 6, pp. 587–597 (1989).

Deshpande et al., *The Journal of Nuclear Medicine.* "Copper–67–Labeled Monoclonal Antibody Lym–1, A Potential Radio–pharmaceutical for Cancer Therapy: Labeling and Biodistribution in RAJI Tumored Mice", vol. 29, No. 2, pp. 217–225 (Feb. 1988).

Franz, J., et al., Abstract from Journal of Nuclear Medicine, Abstract No. 553, vol. 26, No. 5 (May 1985).

Meares, Claude F., Protein Tailoring for Food and Medicine Uses edited by R. E. Feeny et al., *"Attaching Metal Ions to Antibodies"*, pp. 339–352 (1986).

Meares et al., *Int. J. Cancer Suppl.*, 2, 99–102 (1988).

Meares et al., *Br. J. Cancer*, 62, 21–26 (1990).

Gansow et al., ACS Symposium Series, No. 241, p. 215, "Generator Produced Bi–212" (1984).

Moi et al., *Anal. Biochem.*, 148, 249–253 (1985).

*Primary Examiner*—Philip I. Datlow
*Attorney, Agent, or Firm*—Mathews, Woodbridge & Collins

[57] ABSTRACT

Triaza macrocycles carrying a $-CH_2COOH$, $-CH_2CONR^6R^7$, $-CH_2P(R^5)O_2H$, or $-CH_2PO_3H_2$ group on two of the three ring nitrogen atoms and a $-CH(L-Z)COOH$, $-CH(L-Z)CONR^6R^7$, $-CH(L-Z)P(R^5)O_2H$, or $-CH(L-Z)PO_3H_2$ group on the third ring nitrogen atom, in which L is an organic linking radical and Z is any group capable of reacting with a thiol, amino, carboxy, hydroxyl, aldehyde, aromatic, or heteroaromatic group, and metal complexes thereof, are useful for imaging, diagnosis, and therapy. A typical embodiment is N-[5-carboxy-5-{4,7-bis-(carboxymethyl)-1,4,7-triazacyclonon-1-yl}pentyl] 3-maleimidopropionamide.

10 Claims, No Drawings

TRIAZA MACROCYCLES

FIELD OF THE INVENTION

This application is a continuation of Ser. No. 07/948,508 filed Sep. 18, 1992, now abandoned, which is a division of Ser. No. 07/817,999, filed Jan. 9, 1992, now abandoned, which in turn is a continuation of Ser. No. 07/601,700 filed Feb. 12, 1990 as PCT/GB90/00219, now abandoned.

This invention relates to functionalised aza macrocycles, to metal complexes thereof, to conjugate compounds containing the functionalised aza macrocycles and metal complexes thereof and to their use in diagnosis and therapy.

BACKGROUND TO THE INVENTION

The attachment of metal ions to proteins, peptides and other, smaller molecules is a fast expanding technology, which has numerous proven and potential applications in research, in industry and, particularly, in medicine.

In recent years, much of the impetus behind the development of this technology has been the ability to link metal ions to antibodies, especially monoclonal antibodies. Such metal labelled antibodies have found a widespread use, especially in medicine, where they have been employed, for example, to target the metal ion to a specific tissue type, both in vitro and in vivo. Thus, metal labelled antibodies have applications in locating specific tissue types (e.g. employing computer-aided tomographic techniques where the metal ion is in some way detectable) and in the treatment of cell disorders (e.g. treating mammalian tumours where the metal ion is a cytotoxic radionuclide).

Conventionally, attachment of the metal ion to a protein such as an antibody has been achieved by complexation by an acyclic chelate such as a substituted diethylenetriaminepentaacetic acid [Gansow O. A. et al, Inorg. Chem., (1986), 25, 2772] or ethylenediaminetetraacetic acid [Meares, C. F. et al, Acc. Chem. Res., (1984), 17, 202] covalently linked to the antibody. Such acyclic complexes however tend to be unstable in vivo either as a result of acid-catalysed decomplexation or competitive chelate binding by $Ca^{2+}$ or $Zn^{2+}$ in serum, or as a result of competition from transferring [Moerlein, S. M. et al, Int. J. Nuc. Mad. Biol., (1981) 8, 277]. The lack of stability can result in uncomplexed metal atoms in the body which have a cytotoxic effect on healthy tissue (e.g. bone marrow) or which markedly reduce the signal-to-noise ratio of an imaging technique.

A possible alternative to the use of acyclic chelates in the labelling of antibodies is the use of macrocyclic ligands, which has been suggested by a number of workers [Gansow O. A. et al. Am. Chem. Soc. Symp. Ser., (1984), 241, 215; UK Patent Specification Publication No. 212264]; International Patent Specifications Nos. WO89/01475 and WO89/01476 and European Patent Specification No. 305320; and Moi M. K. et al, Anal. Biochem., (1985), 148, 249–253].

We have now found a new class of functionalised aza macrocycles, members of which are able to form kinetically inert complexes with metal ions. The macrocycles of the invention are particularly useful for attachment to proteins, especially antibodies, to provide conjugate compounds capable of binding metals to give complexes which are advantageously stable in vivo.

Thus, according to one aspect of the present invention we provide a compound of general formula (1);

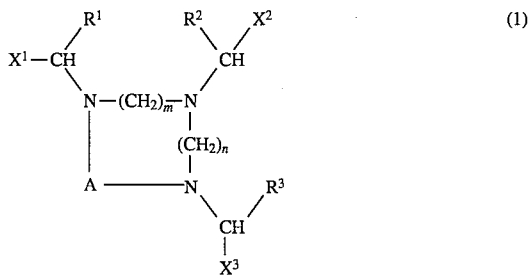

wherein

A is a group —$(CH_2)$— or —$(CH_2)_pN(R)(CH_2)_q$— where R is a group —$CH(R^4)X^4$;

m, n, p, and q, which may be the same or different, is each an integer 2 or 3;

$R^1$, $R^2$, $R^3$ and $R^4$ which may be the same or different, is each a group —$CO_2H$, —$P(R^5)O_2H$ (where $R^5$ is a hydrogen atom or an alkyl or alkoxy group), —$PO_3H_2$ or —$CONR^6R^7$ (where $R^6$ and $R^7$, which may be the same or different is each a hydrogen atom or an alkyl group);

$X^1$, $X^2$, $X^3$ and $X^4$, which may be the same or different, is each a hydrogen atom or an alkyl group, or a linker group, with the proviso that at least one of $X^1$, $X^2$, $X^3$ or $X^4$ is a linker group; and protected derivatives and metal complexes and/or salts thereof.

It will be appreciated that formula (1) [and, where appropriate, the following formulae herein], is intended to cover all stereoisomers of the compounds concerned, including mixtures thereof.

In the compounds of formula (1), it will be appreciated that the nature of the linker group may be varied widely without substantially affecting the usefulness of the compounds. Thus the linker may be any organic radical containing at least one reactive functional group or a protected derivative thereof. Thus the linker may be a group of formula —L—Z, where L is an optionally substituted polyvalent, especially bivalent, radical of an aliphatic, aromatic or araliphatic compound, and Z is a reactive functional group. If desired, more than one functional group Z may be attached to the group L. The group L may be for example an optionally substituted aliphatic hydrocarbyl chain, optionally interrupted by one or more heteroatoms selected from —O— or —S— or by one or more —$N(R^8)$— (where $R^8$ is a hydrogen atom or a $C_{1-6}$alkyl group), —$CON(R^8)$—, —$N(R^8)CO$—, cycloaliphatic, aromatic, or heteroaromatic groups. In the above definition, and in the same context whenever it appears below, the term "interrupted by" as applied to cycloaliphatic or aromatic groups is to be understood to also mean that these particular groups may additionally be present linked to the terminal carbon atom of the hydrocarbyl chain represented by L, at the opposite end of the chain to the carbon atom attached to the macrocycle.

Thus, for example, L may be an optionally substituted straight or branched $C_{1-20}$alkylene, $C_{2-20}$alkenylene, or $C_{2-20}$alkynylene chain, optionally interrupted by one or more —O— or —S— atoms or $C_{5-8}$cycloalkylene (e.g. cyclopentylene or cyclohexylene), $C_{6-12}$aromatic (e.g. phenylene or substituted phenylene), $C_{5-10}$heteroaromatic (e.g. furanyl, pyridyl), —$N(R^8)$—, —$CON(R^8)$— or —$N(R^8)CO$— groups.

Examples of substituents which may be present on the chain L include halogen atoms, e.g. fluorine, chlorine, bromine, or iodine atoms or groups selected from $C_{1-6}$alkoxy (e.g. methoxy or ethoxy), hydroxy, nitro, —N(R$^9$)(R$^{10}$), [where R$^9$ is a hydrogen atom or a $C_{1-6}$alkyl group and R$^{10}$ is a $C_{1-6}$alkyl group; e.g. —NHCH$_3$ or —N(CH$_3$)$_2$], or substituted amido, e.g. a group of formula —(CH$_2$)$_d$CON(R$^{11}$)(R$^{12}$) [where d is zero or an integer 1 to 4 inclusive, R$^{11}$ is a hydrogen atom or a $C_{1-6}$alkyl group, e.g. methyl and R$^{12}$ is an optionally substituted $C_{1-6}$alkyl group].

Substituted alkyl groups represented by R$^{11}$ include for example $C_{1-6}$alkyl groups substituted by one or more halogen atoms, or nitro, amino or hydroxy groups.

The reactive functional group represented by Z may be any group capable of reacting with a thiol, amino, carboxyl, hydroxyl, aldehyde, aromatic or heteroaromatic group. Aromatic groups include, for example, phenolic groups. Heteroaromatic groups include for example imidazolyl groups.

Thus, Z may be, for example, a halogen atom, for example a chlorine, bromine or iodine atom, or a group selected from OH, —SH, —NH2, hydrazine (—NHNH$_2$), or a derivative thereof, [for example —N(CH$_3$)NH$_2$, —NHCONNHN$_2$, —NHCSNHNH$_2$, or phenyl hydrazine], —NCO, —NCS, —COR$^{13}$, [where R$^{13}$ is a halogen atom such as a chlorine or bromine atom, or a N$_3$, $C_{1-6}$alkoxy, e.g. methoxy, $C_{6-12}$aryloxy (e.g. nitrophenyloxy or dinitrophenyloxy) imidyloxy (e.g. succinimidyloxy) or imidazolyoxy group], imide, e.g. maleimide, a vinyl group of formula —Het$^1$—C(Het$^2$)=CH$_2$ (where Her$^1$ and Het$^2$, which may be the same or different, is each a nitrogen containing heterocyclic group, e.g. a pyridyl group or Het$^1$ is a nitrogen containing heterocyclic group and Het$^2$ is a hydrogen atom), for example a vinyl pyridyl group of formula

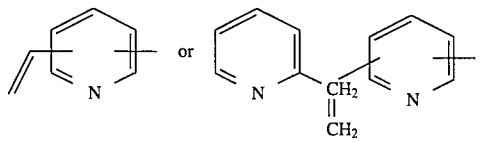

especially

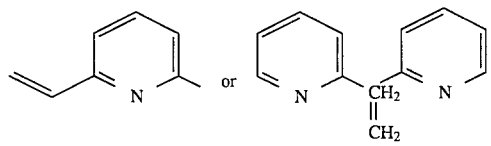

or a dione of formula

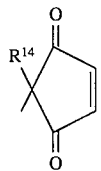

(where R$^{14}$ is a $C_{1-4}$alkyl e.g. methyl group).

Alkyl groups represented by the groups X$^1$, X$^2$, X$^3$, X$^4$, R$^5$, R$^6$ or R$^7$ include $C_{1-6}$alkyl groups such as methyl or ethyl groups.

Metal complexes of the compounds of formula (1) in which A is —(CH$_2$)$_p$ N(R)(CH$_2$)$_q$— include complexes wherein the metal is di- or tripositive and has a coordination number 6 or greater, especially 8. Examples of such metals include indium (In), copper (Cu), lead (Pb), bismuth (Bi), yttrium (Y), terbium (Tb), gallium (Ga), gadolinium (Gd) and scandium (Sc). In, Y, Ga, Tb, Gd, and Sc are preferred, particularly In, Y, Gd, and Ga. In general the metal is preferably a radioactive isotope. Yttrium, especially $^{90}$Y, is particularly preferred.

Metal complexes of the compounds of formula (1) in which A is —(CH$_2$)$_p$— include complexes wherein the metal is di- or tripositive and has a coordination number from 2 up to 6, especially 6. Examples of such metal(s) include indium (In), copper (Cu), lead (Pb), bismuth (Bi), colbalt (Co) and gallium (Ga). In, Ga, Co and Cu are preferred, particularly In and Ga. In general the metal is preferably a radioactive isotope. Indium, especially $^{111}$In, is particularly preferred.

In general, optimum binding of the metal to the compounds of formula (1) may be achieved by selection of the ring size and where appropriate by adjusting the potential coordination number by choice of the group R$^1$, R$^2$, R$^3$ R$^4$.

Protected derivatives of compounds of formula (1) include compounds wherein R$^1$, R$^2$, R$^3$, and/or R$^4$ is a protected carboxyl group, for example a carboxylic ester group e.g. a group —CO$_2$Alk (where Alk is an alkyl group such as methyl or ethyl); and/or wherein the linker group contains one or more protected groups, e.g. protected amino groups.

Salts of the compounds of formula (1) include salts with bases, e.g. sodium or potassium salts, or acid addition salts such as hydrobromides or hydrochlorides. Pharmaceutically acceptable salts are particularly preferred.

A particularly useful group of compounds according to the invention is that of formula (1) wherein A is —(CH$_2$)$_p$— or —(CH$_2$)$_p$N(R)(CH$_2$)$_q$— and m, n, p, and q is each an integer 2.

A further preferred group of compounds of formula (1) wherein A is —(CH$_2$)$_p$— or —(CH$_2$)$_p$N(R)(CH$_2$)$_q$— is that wherein R$^1$, R$^2$, R$^3$, and R$^4$ is each a —CO$_2$H group.

Yet a further preferred group of compounds of formula (1) wherein A is —(CH$_2$)$_p$— or —(CH$_2$)$_p$N(R)(CH$_2$)$_q$— is that wherein one or two of X$^1$, X$^2$, X$^3$ and X$^4$ is a linker group and the remainder are alkyl groups or, especially, hydrogen atoms.

One group of compounds of formula (1) has the formula (1a):

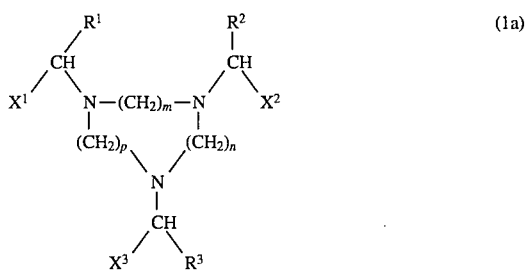

wherein m, n, p, R$^1$, R$^2$, R$^3$, X$^1$, X$^2$ and X$^3$ are as defined for formula (1); and protected derivatives and metal complexes and/or salts thereof.

Indium complexes of the compounds of formula (1a) are particularly preferred.

Particularly important compounds of formula (1a) are those of formula (1b)

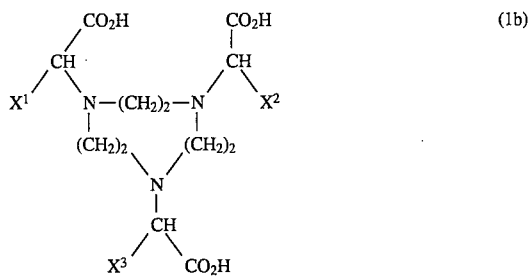
(1b)

wherein one or two of $X^1$, $X^2$, or $X^3$ is a linker group and the remainder are hydrogen atoms; and protected derivatives and metal complexes and/or salts thereof.

Indium complexes of the compounds of formula (1a) are particularly preferred.

Another group of compounds of formula (1) has the formula (1c):

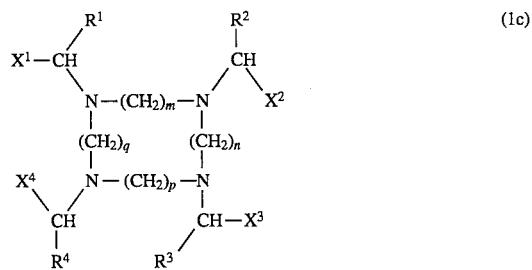
(1c)

wherein m, n, p, q, $R^1$, $R^2$, $R^3$, $R^4$, $X^1$, $X^2$, $X^3$ and $X^4$ are as defined for formula (1); and protected derivatives and metal complexes and/or salts thereof.

Yttrium complexes of the compounds of formula (1c) are particularly preferred.

An important group of compounds of formula (1c) are those of formula (1d)

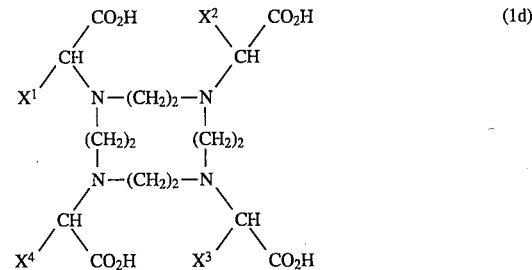
(1d)

wherein one or two of $X^1$, $X^2$, $X^3$ or $X^4$ is a linker group and the remainder are hydrogen atoms; and protected derivatives and metal complexes and/or salts thereof.

Yttrium complexes of the compounds of formula (1a) are particularly preferred.

The compounds of formula (1) and the metal complexes and/or salts thereof have a diagnostic use as imaging agents in vitro and in vivo. The compounds of formula (1) and the metal complexes and/or salts thereof are also cytotoxic agents and may be used in the treatment of abnormal cell disorders, for example in the treatment of tumours. For use as diagnostic and/or therapeutic agents, the compounds of formula (1) may be employed using conventional methods, (e.g. for formulation and presentation) already in use for metal complexing agents.

For application of the compounds of formula (1) as imaging or cytotoxic agents, it is generally preferable to couple the compounds to other molecules such a proteins, especially antibodies, peptides or carbohydrates to form conjugate compounds, and the compounds of formula (1) are particularly well adapted for use in this respet.

Thus, according to a further aspect of the invention, we provide a conjugate compound which comprises a compound of formula (1), or a metal complex and/or salt thereof, coupled to a protein, peptide or carbohydrate.

The compound of formula (1) may be coupled through any thiol, amino, carboxyl, hydoxyl, aldehyde, aromatic or heteroaromatic group present in the protein, peptide or carbohydrate.

In a preferred aspect of the invention, we provide a conjugate compound which comprises a compound of formula (1) or a metal complex and/or salt thereof, coupled to an antibody.

It is to be understood that conjugate compounds according to the invention may contain more than one molecule of a compound of formula (1) couple to any one protein, peptide or carbohydrate molecule.

Particularly useful conjugate compounds according to the invention are those comprising a compound of formula (1b) or formula (1d) or a metal complex and/or salt thereof, coupled to an antibody. The indium and yttrium complexes of these conjugates are especially important.

The compounds of formula (1) and conjugate compounds of the invention may be formulated for use in accordance with conventional practice. Thus according to a further aspect of the invention we provide a composition comprising a compound of formula (1); or a conjugate compound comprising a compound of formula (1) coupled to a protein, peptide or carbohydrate, or a metal complex and/or salt thereof, together with one or more pharmaceutically acceptable carriers.

Particularly suitable compositions according to the invention are those adapted for parenteral administration, especially by injection or infusion. Suitable formulations of this type include suspensions solutions or emulsions of the compound or conjugate in oily or aqueous vehicles, and may contain formulatory agents such as suspending, stabilising and/or dispersing agents. Alternatively the compound or conjugate may be in powder form for reconstitution with a suitable vehicle, e.g. sterile pyrogen-free water before use. If desired the compound or conjugate may be presented in unit dosage form, and/or together with one or more active ingredients or agents. Suitable formulations of this type include solutions of the compounds of formula (1) in isotonic saline.

The quantities of compounds of formula (1) used in formulations according to the invention will vary according to the intended cell target, but may be easily determined in accordance with conventional practice for reagents of this type.

Compounds of the invention may be prepared by the following processes wherein the groups and symbols $R^1$, $R^2$, $R^3$, $R^4$, m, n, p, q, $X^1$, $X^2$, $X^3$ and $X^4$ are as defined for formula (1) except where stated otherwise. Where a metal complex is desired as a final product, the complexation with a metal atom may be carried out as a final step in the production process, as described below for the complexation of compounds of formulae (1), or alternatively it may be desirable to complex the metal at an earlier stage in the process, providing of course that the requisite macrocycle structure is present. In the following processes, it may be desirable to use starting materials in which functional groups in the linker group are in a protected state, or which contain a precursor of the group, as discussed below.

Thus according to a further aspect of the invention a compound of formula (1) wherein at least one of $X^1$, $X^2$, $X^3$ and $X^4$ is other than a linker group, or a protected derivative or a metal salt thereof may be prepared by reaction of a compound of formula (2):

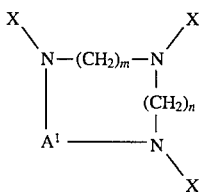

[wherein $A^1$ is $-(CH_2)_p-$ or $-(CH_2)_pN(H)(CH_2)_q-$ a least one of the groups X is a hydrogen atom and the remainder is each a group $-CH(R^1)X^1$, where $R^1$ is as previously defined and $X^1$ is a linker group or a protected derivative thereof] with a compound $DCH(R^2)X^2$ (where $X^2$ is as defined for formula (1), but is not a linker group, or a protected derivative thereof, and D is a displaceable group, for example a halogen atom such as a bromine atom) followed, where necessary, by removal of any protecting group.

The reaction may be performed in a solvent such as water or an organic solvent such as a nitrile, e.g. acetonitrile, or an alcohol, e.g. ethanol, or an amide, e.g. dimethylformamide, in the presence of a base such as an alkali metal carbonate or hydroxide, e.g. sodium, potassium or caesium carbonate, or sodium, potassium or lithium hydroxide, at an elevated temperature e.g. the reflux temperature.

Protecting groups may be removed using conventional procedures depending on the nature of the protected group. Thus, for example esters may be hydrolysed to the corresponding acids using a base, for example an alkali metal hydroxide such as sodium or potassium hydroxide.

Where metal complexes of formula (1) are required (or any other suitable macrocylic intermediate described herein) these may be prepared by treating the compound with a metal salt (for example a metal halide) in an appropriate solvent for example an aqueous or non aqueous solvent, (e.g. acetonitrile, acetone, propylene carbonate, dimethylformamide or dimethylsulphoxide) at any suitable temperature from 0° C. to 100° C. such as 10° C. to 80° C. e.g. around 60° C.

A conjugate compound according to the invention may be prepared by reaction of a compound of formula (1) or a metal complex thereof with a protein, peptide or carbohydrate in a aqueous solvent, for example an inorganic buffer such as a phosphate buffer at an appropriate temperature.

Salts of compounds of formula (1) and their metal complexes may be prepare by conventional means, for example by reaction with an appropriate base or acid in a suitable aqueous solvent.

Intermediates of formula (2) may be prepared by reaction of a compound of formula (3)

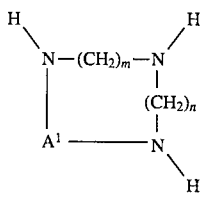

with a compound $DCH(R^1X^1$ (where $X^1$ is a linker group or a protected derivative thereof) in the presence of a base in a suitable solvent at an elevated temperature as just described for the preparation of compounds of formula (1). By varying the molar ratio of the compound of formula (2) and the compound $DCH(R^1)X^1$ such that the latter is increased relative to the former, (for example from around 2:1 to 1:1 and further) compounds of formula (2) containing more than $-CH(R^1)X^1$ group as just defined may be prepared.

Intermediates of formula (3) are either known compounds or may be prepared from known starting materials using methods analogous to those used for the preparation of the known compounds.

The following Examples illustrate the invention.

EXAMPLE 1

(a) To a stirred solution of 1,4,7,10-tetraazacyclododecane (0.057 g) in dry dimethylformamide (5 ml) was added anhydrous potassium carbonate (0.05 g). To this mixture at 80° C. under nitrogen was added 2-bromo-6-benzamidoethyl hexanoate (0.113 g) in dimethylformamide (5 ml) over 2 hours. HPLC analysis revealed that after 2 days reactions was essentially complete to give, after removal of dimethylformamide a single major product [CM-300; gradient elution; t=0: A=80%, B=0%, C=20%; t=5 min: A=60%, B=20%, C=20%; t=10 min: A=0%, B=80%, C=20% (with A=$H_2O$, B=1M ammonium acetate (pH 5.6), C=$CH_3CN$) flow rate=1.4 ml:$min^{-1}$]. Retention time=7.5 min. m/e (CI) 433 ($M^++1$) $\delta_H$(CDCl$_3$) 1.25 (3H, t, $CO_2CH_2\underline{CH}_3$), 1.45–1.79 (6H, mult, $\underline{CH_2CH_2CH_2}CH_2NH$), 2.39–3.13 (16H m·ring $CH_2$'s) 3.32–3.50 (3H, m, $CONH\underline{CH}_2$ and $OCOC\underline{H}$), 4.14 (2H, q, $CH_2O$), 7.37–7.50 (4H, m, atom plus NHCO), 7.79 (2H, d+d ortho atom H).

(b) The compound prepared in part (a) was not isolated but was redissolved in dimethylformamide (5 ml). To this solution was added dry potassium carbonate (0.15 g) and at 80° C. ethyl bromoacetate (0.165 g) was added to a solution in dimethylformamide (2 ml) over 15 min. Reaction was complete in 4 hours [HPLC analysis gave a major product at t=6.19 min under the conditions defined in part (a)]. After removal of dimethylformamide in vacuo the residue was chromatographed on neutral alumina (0.5%.methanol/$CH_2Cl_2$ - 5% methanol/$CH_2Cl_2$) to yield as a pale oil the compound of formula (1) wherein A is $-(CH_2)_p(R^4)(CH_2)_q-$, m, n, p and q is each an integer 2; $R^1$, $R^2R^3$ and $R^4$ is each a group $-CO_2CH_2CH_3$; $X^1$, $X^3$ and $X^4$ is each a hydrogen atom; and $X^2$ is a group $-(CH_2)_4NHCOPh$ (where Ph is phenyl). m/e (DCE, ethanol) 692 ($M^++1$). $\delta_H$(CDCl$_3$) 1.25 (12H, t+t+t, Me), 1.40–1.90 (6H, mult, $CH_2CH_2CH_2CH_2NHCO$), 2.13–3.20 (16H, mult, ring $\underline{CH_2}$), 3.30–3.55 (9H, mult, $CH_2CO+CHCO+CH_2NHCO$), 4.08–4.18 (8H, mult., $OCH_2$) 7.40 (3H, brd, atom H), 7.94–8.07 (3H, brd+mult., ortho CH+NHCO).

EXAMPLE 2

A solution of the compound of Example 1(b) (30 mg) in hydrochloric acid (6m, 10 ml) was heated to reflux for 36 h. After cooling, and washing with diethyl ether (3×3 ml), the removal of solvent under high vacuum yielded the compound of formula (1) wherein A is $-(CH_2)_nN(R)(CH_2)_q-$, m, n, p and q is each an integer 2, $R^1$, $R^2$, $R^3$ and $R^4$ is each a group $-CO_2H$, $X^1$, $X^3$ and $X^4$ is each a hydrogen atom and $X^2$ is a group $-(CH_2)_4NH_2-$ as its tetrahydcochloride (28 mg). $\delta_H$(D$_2$O) 1.64 (6H, br. mult., $CH_2C$), 2.93–4.16 (25 H, mult. br., $CH_2N+$ CHN), m/e (negative FAB, m-nitrobenzyl alcohol) 476 ($M^-$), 475 ($M^-$-1).

EXAMPLE 3

To a solution of the compound of Example 2 (9.5 mg) in dry DMF (200 µl) was added a solution of N-succinimidyl- 3-maleimidopropiorate (14.0 mg) in dry DMF (60 μl), and N-methyl morpholine (40 mg) yielding a slight precipitate. Addition of MilliQ water (0.003 ml) dissolved the precipitate and the mixture was held at 30° C. for 24h. After removal of solvent under reduced pressure, the residue was purified on reverse-phase HPLC (Spherisorb 50DS2) to yield as a colourless glass and compound of formula (1) corresponding to the compound of Example 2 except that $X^2$ is a group

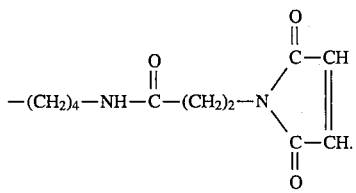

m/e (FAB, m-nitribenzylalcohol) 628 ($M^+$+1), 552, 493,409. $\delta_H$($D_2O$) 6.85 (2H, s, CH═CH), 3.96–3.91 (7H, mult, $CH_2N$+CHN), 3.85 3.05 (20 H mult. br. $CH_2N$+$CH_2$NHCO+$CH_2$NCO), 2.50 (2H, t, J=6.4, $CH_2$CONH), 1.65 (6H, mult, $CH_2$C). Rt=8.9 min (Spherisorb ODS2, 1.4 ml min$^{-1}$, t=0, 95% 0.1% TFA in $H_2O$, 5% 0.1% TFA in $CH_3$CN t=20, 5% 0.1% TFA in $H_2O$, 95% 0.1% TFA in $CH_3$CN).

To a solution of the tetraacid (10 μmol) in ammonium acetate buffer (90 μl, pH 6.0) was added 5 μl of an $^{90}Y$ solution (2 μCi) and the mixture was incubated for 0.5 h at 37° C. Reaction was quenched by addition of a 20 fold excess of diethylenetriamindpentaacetic acid (DTPA) and the relative amounts of 90Y complex and 90Y-DTPA determined by HPLC radiometry (AX-300 anion exchange: eluant 0.2 M $NH_4OAC$, 10% $CH_3CN$). A radiolabelling yield of 77% was calculated. In the presence of a 500 fold excess of DTPA at 25° C. the relative concentration of the radiolabelled complex was measured at 24, 48 and 72 h and seen not to diminish (±2%).

EXAMPLE 4

To a solution of 1,4,7-triazacyclononane (0.104 g) in dry dimethylformamide (5 ml) was added potassium carbonate (0.117 g) followed by 2-bromo-6-benzemidoethyl hexanoate (0.276 g) as a solution in dimethylformamide (3 ml). After stirring for 50 h at 50° C., the cooled solution was filtered and solvent removed under reduced pressure to give a colourless oil, m/e (DCI, ethanol) 652 ($M^+$+1); HPLC [CH300; 2 major peaks (λmax 235 nm) at 2.4 and 4.7 min with t=0: A=70%, B=10%, C=20%,; t=10 min: A=0%, B=80%, C=20% (A=$H_2O$, B=1 M ammonium acetate, C=$CH_3CN$)].

To a solution of the crude oil in dry ethanol (2 ml) was added caesium carbonate (0.163 g) and ethyl bromoacetate (0.083 g). The mixture was stirred for 20 hours at 60° C. when the solution was cooled, filtered and solvent removed to yield a pale yellow residue which was chromatographed on neutral alumina (1% methanol/$CH_2Cl_2$) to give as a colourless oil [Rf=0.5(2.5% methanol/$CH_2Cl_2$)] the compound of formula (1) wherein A is —($CH_2$)$_p$, m, n and p is each an integer 2, $R^1$, $R^2$ and $R^3$ is each a group —$CO_2CH_2CH_3$, $X^1$ and $X^2$ is each a group —($CH_2$)$_4$NHCOPh (where Ph is phenyl) and $X^3$ is a hydrogen atom. m/e (DCI, ethanol) 738 ($M^+$+1), 621, 420. $\delta_H$(CDCl$_3$, 298 K) 1.24 (9H, t, $CH_3$, J=7.1 Hz), 1.29–1.68 (12 H, mult., $CH_2CH_2CH_2CH_2$NH), 2.77–3.46 (20 H, mult., $CH_2N$, CHN), 4.11 (6H, q+q, $CH_2O$), 6.66 (2H, brs, NHCO), 7.42 (6H, mult., atom H), 7.79 (4H, dd, ortho CH).

EXAMPLE 5

The compound of formula (1) wherein A is —($CH_2$)$_p$—, m, n and p is each an integer 2, $R^1$, $R^2$ and $R^3$ is each a group —$CO_2CH_2CH_3$, $X^1$ is a group —($CH_2$)$_4$NHCOPh (where Ph is phenyl) and $X^2$ and $X^3$ is each a hydrogen atom was prepared using the methods of Example 4 except 1,4,7-triazacyclononane and 2-bromo-6-benzamidoethyl hexanoate were used in a 2:1 molar ratio. The product was purified by column chromatography on neutral alumina to yield a colourless oil, Rf=0.4 (2% methanol/$CH_2Cl_2$). m/e (DCI, ethanol) 563 ($M^+$+1). $\delta_H$ (CDCl$_3$, 298K) 1.25 (1H, t+t, $CH_3$), 1.28–1.69 (6H, mult., $CH_2CH_2CH_2CH_2$-NHCO), 2.76–3.02 (12 H, mult., $CH_2$N ring), 3.22–3.54 (7 H, mult., $CH_2$NHCO +C$\underline{H}$CO+$CH_2$CO), 4.13 (6 H, q, $CH_2$O), 6.67 (1 $\underline{H}$, brs, NHCO), 7.40 (3H, mult. arom CH), 7.79 (12 H, brd, ortho CH).

EXAMPLE 6

N, $N^1$-bis(2-(N-(3-maleimidopropanoyl)-4-aminobutyl)carboxymethyl)-N"-carboxymethyl- 1,3,7-triazacyclononane, (10 mg) was prepared from the compound of Example 4 (38 mg) using a similar procedure to that described for the preparation of the compound of Example 3 from the compound of Example 1.

m/e (FAB, p-NBA matrix) 748($M^+$+1) 596; $\delta_H$ ($D_2O$) 6.85 (4H, S, CH═CH) 3.96 (4H, m, $CH_2CO_2$) 3.79 (8 H, m, C$\underline{H}_2$NCO and C$\underline{H}_2$NHCO) 3.10–3.25 (12 H, m, $CH_2$N) 2.49 (4 H, t, J 6.3 H$_2$, $CH_2$CONH) 1.82 (3H, m, $CH_2$—C) 1.46 (3H, m $CH_2$—C).

EXAMPLE 7

N-(2-(N-(3-maleimidopropanoyl)-4-aminobutyl)carboxymethyl)-N', N"-bis (carboxymethyl0-1,4,7-triazacyclononane, was prepared from the compound of Example 5 using a similar procedure to that described for the preparation of the compound of Example 3 from the compound of Example 1.

m/e (FAB, p-NBA matrix) 526($M^+$+1) 453, 391, 307; $\delta_H$ ($D_2O$) 6.85 (2H, S, CH═CH) 3.95 (5 H, m, $CH_2CO_2$) 3.79 (4 H, m, C$\underline{H}_2$NCO and C$\underline{H}_2$NHCO) 3.00–3.50 (12 H, m, $CH_2$N) 2.49 (2H, t, J 6.2 H$_2$, $CH_2$CONH) 1.69 (3 H, m, $CH_2$-C) 1.46 (3H, m $CH_2$-C).

We claim:

1. A compound of the formula:

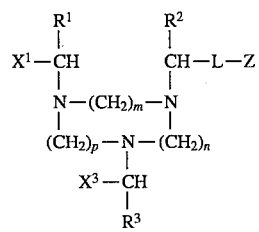

wherein:
  each of m, n, and p, independently of the others, has a value of 2 or 3;
  each of $R^1$, $R^2$, and $R^3$, independently of the other, is —COOH, —CONR$^6$R$^7$, —P(R$^5$)O$_2$H, or —PO$_3$H$_2$;
  each of $R^5$, $R^6$, and $R^7$, independently of the other, is hydrogen or alkyl;

each of $X^1$ and $X^3$, independently of the other, is hydrogen, alkyl, or —L—Z;

Z is a group capable of reacting with a thiol, amino, carboxyl, hydroxy, aldehyde, aromatic group, or heteroaromatic group on a antibody; and L is an organic linking radical.

2. A compound according to claim 1 having the formula:

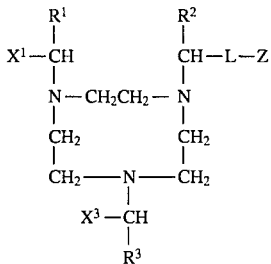

wherein each of $R^1$, $R^2$, $R^3$, $R^5$, $R^6$, $R^7$, $X^1$, $X^3$, Z, and L is as therein defined.

3. A compound according to claim 2 wherein each of $R^1$, $R^2$, and $R^3$ is —COOH.

4. A compound according to claim 3 wherein each of $X^1$ and $X^3$ is hydrogen.

5. A compound according to claim 1 wherein L is an optionally substituted hydrocarbyl chain which optionally includes one or more members selected from the group consisting of —O—, —S—, —N ($R^8$)—, —CON($R^8$)—, —N ($R^8$)CO—, a cycloaliphatic ring, an aromatic ring, and a pyridine ring, in which $R^8$ is hydrogen or alkyl of 1 to 6 carbon atoms.

6. A compound according to claim 1 wherein Z is selected from the group consisting of halo, hydroxy, thiol, amino, hydrazino, —N═C═O, —N═C═S, —$COR^{13}$, imido vinylpyridinyl, [1-(pyridyl)eth-1-en-1-yl]pyridinyl, and 2-$R^{14}$-cyclopent- 4-ene-1,3-dione, in which $R^{13}$ is halo, azido, alkoxy of 1 to 6 carbon atoms, aryloxy of 6 to 12 carbon atoms, imidyloxy, or imidazolyloxy and $R^{14}$ is alkyl of 1 to 4 carbon atoms.

7. A complex of a compound according to claim 1 with a di- or tripositive metal atom having a coordination number of from 2 to 6.

8. A complex according to claim 7 wherein the metal is indium, copper, lead, bismuth, cobalt, or gallium.

9. A complex according to claim 7 wherein the metal is indium.

10. A compound according to claim 1 wherein Z is amino, 6-vinylpyridin-1-yl, 6-[1-(1-pyridyl)eth-1-en-1-yl]-pyridin-1-yl, or 2-$R^{14}$-cyclopent-4-ene-1,3-dione in which $R^{14}$ is alkyl of 1 to 4 carbon atoms.

* * * * *